United States Patent [19]

von Bonin et al.

[11] Patent Number: 4,570,622

[45] Date of Patent: * Feb. 18, 1986

[54] CONSTRUCTIONAL MATERIAL

[75] Inventors: Wulf von Bonin; Ulrich von Gizycki; Kuno Wagner, all of Leverkusen; Dietmar Schäpel, Cologne, all of Fed. Rep. of Germany

[73] Assignee: Bayer Aktiengesellschaft, Leverkusen, Fed. Rep. of Germany

[ * ] Notice: The portion of the term of this patent subsequent to Oct. 18, 2000 has been disclaimed.

[21] Appl. No.: 545,013

[22] Filed: Oct. 24, 1983

Related U.S. Application Data

[60] Division of Ser. No. 336,206, Dec. 31, 1981, Pat. No. 4,411,262, which is a continuation of Ser. No. 898,753, Apr. 21, 1978, abandoned, which is a continuation of Ser. No. 782,656, Mar. 30, 1977, abandoned, which is a continuation-in-part of Ser. No. 684,131, May 7, 1976, abandoned.

[51] Int. Cl.$^4$ .................................................. A61F 5/04
[52] U.S. Cl. ........................................ 128/90; 428/266
[58] Field of Search ............... 128/90, 155, 156, 89 R, 128/91 R; 428/266

[56] References Cited

U.S. PATENT DOCUMENTS

| | | | |
|---|---|---|---|
| 3,317,481 | 5/1967 | Youker | 260/77.5 |
| 3,373,741 | 3/1968 | Hill et al. | 128/94 |
| 3,630,194 | 12/1971 | Boardman | 128/90 |
| 3,635,904 | 1/1972 | Briggs et al. | 260/77.5 AA |
| 3,652,508 | 3/1972 | Segur et al. | 260/77.5 AA |
| 3,656,475 | 4/1972 | Hanrahan, Jr. | 128/90 |
| 4,131,114 | 12/1978 | Kirkpatrick et al. | 128/90 |
| 4,411,262 | 10/1983 | von Bonin et al. | 128/90 |

FOREIGN PATENT DOCUMENTS 2353212 10/1973 Fed. Rep. of Germany.
6903236 4/1974 Netherlands.

*Primary Examiner*—John D. Yasko
*Attorney, Agent, or Firm*—Gene Harsh; Lawrence S. Pope

[57] ABSTRACT

The present invention relates to a constructional material which is stable in storage and which is kept under moisture-free conditions and which comprises a substrate and a reactive one-component system which hardens on exposure to air by reaction with moisture. The present invention also relates to a process for the production of a constructional material which is stable in storage.

17 Claims, No Drawings

CONSTRUCTIONAL MATERIAL

CROSS REFERENCE TO RELATED APPLICATIONS

This application is a divisional of application Ser. No. 336,206 filed Dec. 31, 1981, now U.S. Pat. No. 4,411,262; which itself is a continuation of application Ser. No. 898,753 filed Apr. 21, 1978 and now abandoned; which is a continuation of application Ser. No. 782,656 filed Mar. 30, 1977 and now abandoned; which is a continuation-in-part of application Ser. No. 684,131 filed May 7, 1976 and now abandoned.

FIELD OF THE INVENTION

This invention relates to novel bandanging and stiffening materials and to a process for their production.

BACKGROUND OF THE INVENTION

It is known in the art to steep woven or non-woven webs or knitted goods of various materials in reactive resins, varnishes or polymer solutions and then, after shaping the textiles to solidify them by a hardening reaction (e.g. irradiation with UV light) or by evaporation of the solvent so that they can be used as a dimensionally stable constructional material. It is also known to impregnate woven, non-woven or knitted fabrics with molten high-molecular weight substances and shape them in the hot state and then allow them to solidify by cooling. Lastly, it is known to coat woven or non-woven webs with inorganic dry materials which are stable in storage; these dry materials subsequently setting when moistened with water and thereby imparting strength to the shaped material.

All these processes, however, have disadvantages which stand in the way of economic convenient and, above all, physiologically harmless application. The impregnated webs either still contain volatile monomers or solvents, which may be undesirable for physiological or safety reasons or are unstable in storage. Additionally, the impregnated webs may require moistening with water or solvents, which must subsequently be removed after application by exposure to heat or by the use of mechanical devices which may, for example, make it impossible or difficult to use them in contact with human skin.

SUMMARY OF THE INVENTION

It has now been found that constructional materials which are stable in storage before their application and do not have the disadvantages mentioned above can be obtained if a preferably porous and flexible substrate is impregnated and/or coated under air-tight conditions with a single-component reactive system which does not contain any significant quantities of volatile constituents and which is subsequently hardened by moisture upon exposure to air.

The substrate which has been treated in this way is packaged under air-tight conditions and in the absence of moisture and is then stable in storage at temperatures up to about 35° C., preferably up to 25° C. It is only when the liquid-viscous or flexible reactive system is exposed to air that it hardens by reaction with moisture and thereby imparts rigidity, strength and cohesion to the constructional material.

DETAILED DESCRIPTION OF THE INVENTION

This invention therefore relates to a constructional material which is stable in storage and which is kept under moisture-free conditions and which comprises a substrate and a reactive one-component system which hardens on exposure to air by reaction with moisture.

The present application also relates to a process for the production of a constructional material which is stable in storage. The constructional material comprises a substrate impregnated and/or coated with a reactive one-component system which hardens on exposure to air by reaction with moisture, characterized in that the substrate is first treated with the reactive system under moisture-free conditions and then packaged in an air-tight container.

The constructional materials according to the invention are, for example, textile sheets such as (gauze) bandages and twine which are impregnated with the one-component reactive systems, and which, when stored under air-free conditions, are stable in storage.

On removal from the air-tight package, the constructional materials can be applied, for example, as a bandage or other dressing and then harden within a short time. It is not only as bandaging materials that they can be used but also for producing containers, filters, and tubes, for binding constructional elements, for the manufacture of decorative or artistic products, for stiffening purposes or as filling or sealing material for joints and cavities.

The substrates used may be non-porous or, preferably, porous sheets or foams of natural or synthetic materials, e.g. polyurethanes. Woven or knitted fabrics or non-woven webs made of natural or synthetic organic or inorganic fibrous materials which have an elastic or only slightly elastic character are particularly suitable, for example, leather, cellulose, glass, polyamide, polyolefine, PVC, polyurethane, rubber, acrylic-, metal-, carbon-, polyimide-, wool-, or polyester fibers. The substrates may, of course, be manufactured either from fibers or from fiber bundles or filaments or foil strips.

Fibrous or filamentary strands or cables, braids etc. are also suitable for use as substrates for the process according to the invention.

The preferred substrates, however, are flexible, sheet-like or strand-like substrates such as foamed plastics sheets, paper, woven glass fabrics, non-woven glass webs and woven, knitted or non-woven webs known per se made of uniform or mixed natural and/or synthetic fibers or filaments such as wool, cotton, aromatic or aliphatic polyamides, polyimides, polyesters, polyacrylonitrile, PVC or polyolefines.

The reactive systems used for the process according to the invention preferably contain less than about 1% by weight of volatile substances which can be removed by evaporation at 12 Torr (1 Torr is equal to 1 mm Hg) and 20° C. in one hour, but they are preferably still tacky and/or have a certain fluidity, shapeability, elasticity, pliability or plasticity so that the substrate impregnated with the reactive system will be in a workable state and have sufficient coherence. The reactive systems should not lose these properties when stored under air-free conditions, but on exposure to air, they should react with moisture to be converted into a rigid, non-tacky or only slightly tacky and no longer fluid and only slightly deformable state so that, for example, a structure made by winding the material according to the invention will have the layers of the winding adhering firmly to each other and will have a stabilized stiff and rigid character.

The reactive systems used in the process according to the invention are generally substances with a viscosity of from about 3,000 to 50,000 cP at 20° C. and, preferably, between about 10,000 and 30,000 cP at 20° C. They contain reactive groups which, optionally in the presence of suitable accelerators or activators, react preferably at ambient temperatures with moisture in the air to form a polymer network or at least undergo an increase in molecular size. These reactive groups may be, for example SiOR-groups or isocyanate groups, where R is a $C_1$–$C_{18}$ alkyl, $C_4$–$C_{18}$ cycloalkyl or a phenyl group.

One variation of this principle is represented by reactive systems which contain an accelerator or reactant which is masked or not effective on its own, but which reacts with moisture to be converted into an active form in which it is capable of undergoing the hardening reaction. Reactive systems of this kind include, for example systems which contain isocyanate groups and ketimines, the ketimines reacting with the moisture of the air to liberate a reactive amine.

The following are examples of classes of reactive substances suitable for the purpose of the invention which are sufficiently fluid in the absence of air and yet contain less than 1% by weight of volatile components as defined above:

(1) silicones or other organic compounds with molecular weights of up to about 10,000 which contain Si-OR-groups, where R is the same as defined immediately above which hydrolize on exposure to atmospheric moisture, whereupon crosslinking or increase in molecular size occurs by condensation of the intermediately formed SiOH-groups;

(2) polyisocyanates or compounds with viscosity below about 50,000 cP at 20° C., preferably polyesters, polyethers, polyamides, polyureas or polyurethanes, which are modified with isocyanate groups in end positions and/or side chains.

Compounds of type (1) have been described, for example, in German Offenlegungsschriften Nos. 2,155,258; 2,155,259 and 2,155,260, in German Patent Application No. P 22 43 628.8, and in U.S. Pat. Nos. 3,895,043 and 3,856,756, incorporated herein by reference. They are silyl-substituted urea or biuret derivatives which can be prepared by reacting an aminoalkyl silane derivative, of the formula:

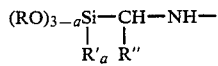

in which
R represents a $C_1$–$C_{18}$ alkyl or $C_4$–$C_{14}$ cycloalkyl group or a phenyl group,
R' represents a $C_1$–$C_{18}$ alkyl, $C_4$–$C_{10}$ cycloalkyl or $C_6$–$C_{10}$ aryl group which may be halogenated or cyano-substituted
R" represents a hydrogen atom or a methyl or phenyl group and
a=0,1 or 2
with a compound which contains uretdione or isocyanate groups; or by reacting a compound of the general formula

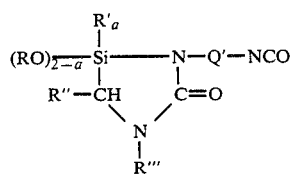

in which R, R', R" and a have the meanings specified above and R''' represent hydrogen or a $C_1$–$C_{18}$ alkyl, $C_4$–$C_{14}$ cycloalkyl or $C_6$–$C_{14}$ aryl group which may be halogenated or cyano-substituted and Q' represents a divalent $C_1$–$C_{18}$-alkyl, $C_1$–$C_{14}$-cycloalkyl or $C_6$–$C_{14}$-aryl or arylalkyl group with a higher molecular weight compound which contains hydroxyl or amino end groups.

The alkoxy silane derivatives used for the process according to the invention are preferably the mixtures described in German Offenlegungsschrift No. 2,138,943 and U.S. Pat. No. 3,793,253, incorporated herein by reference, because these can be applied solvent-free because of their viscous liquid consistency. The basic constituents of these mixtures are 5-silaimidazolidones-(2) of the formula

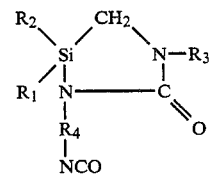

in which
$R_1$ and $R_2$ which may be the same or different, represent alkyl or alkoxy groups or may together represent a bisoxyalkylene group as described in U.S. Pat. No. 3,793,253,
$R_3$ represents hydrogen or an alkyl or aryl group and
$R_4$ represents a divalent (cyclo) aliphatic, araliphatic or aromatic group which may contain hetero atoms.

The compounds mentioned under (2) are preferably used in the present invention and may be either modified or unmodified polyisocyanates or preferably, reaction products of polyisocyanates with compounds which contain at least two hydrogen atoms that are reactive with isocyanates. Apart from compounds which contain amino, thiol or carboxyl groups, the compounds of this kind are preferably water and high-molecular weight or low-molecular weight polyhydroxyl compounds. Suitable higher molecular weight polyhydroxyl compounds are e.g. polyesters, polyethers, polythioethers, polyacetals, polycarbonates and polyester amides containing at least two, preferably two to four hydroxyl groups, of the kind known per se for the production both of homogeneous and of cellular polyurethanes.

Suitable polyester with hydroxyl groups are, for example, the reaction products of polyhydric, preferably dihydric alcohols to which trihydric alcohols may be added, and polybasic, preferably dibasic carboxylic acids. Instead of free polycarboxylic acids, the corresponding polycarboxlic acid anhydrides or corresponding polycarboxylic acid esters of lower alcohols or mixtures thereof may be used for preparing the polyesters. The polycarboxylic acids may be aliphatic, cycloaliphatic, aromatic and/or heterocyclic and may be substituted, e.g. with halogen atoms and/or unsaturated. The following are mentioned as examples: succinic acid; adipic acid; suberic acid; azelaic acid; sebacic acid; phthalic acid; isophthalic acid; trimellitic acid; phthalic acid anhydride; tetrahydrophthalic acid anhydride; hexahydrophthalic acid anhydride; tetrachlorophthalic acid anhydride; endomethylene tetrahydrophthalic acid anhydride; glutaric acid anhydride; maleic acid; maleic acid anhydride; fumaric acid; dimeric and trimeric fatty acids such as oleic acid which may be mixed with monomeric fatty acids; dimethyl terephthalate and bis-glycol terephthalate. Suitable polyhydric alcohols are e.g. ethylene glycol; propylene-1,2- and -1,3-glycol; butylene-1,4- and -2,3-glycol; hexane-1,6-diol; octane-1,8-diol; neopentyl glycol; cyclohexane dimethanol (1,4-bis-hydroxymethyl cyclohexane); 2-methyl-propane-1,3-diol; glycerol; trimethylolpropane; hexane-1,2,6-triol; butane-1,2,4-triol; trimethylolethane; pentaerythritol; quinitol; mannitol and sorbitol; methyl glycoside; diethylene glycol; triethylene glycol; tetraethylene glycol; polyethylene glycols; dipropylene glycol; polypropylene glycols; dibutylene glycol and polybutylene glycols. The polyesters may contain a proportion of carboxyl groups in end positions. Polyesters of lactones such as e-caprolactone or hydroxy carboxylic acids such as ω-hydroxycaproic acid may also be used.

The polyethers with at least two, generally two to eight, and preferably, two or three hydroxyl groups which may be used, are also known per se and may be prepared e.g. by polymerizing epoxides such as ethylene oxide, propylene, oxide, butylene oxide, tetrahydrofuran, styrene oxide or epichlorohydrin, each with itself, e.g. in the presence of boron trifluoride, or by their addition, either as mixtures or successively, to starting components which contain reactive hydrogen atoms such as water, alcohols or amines, e.g., ethylene glycol, propylene-1,3- or -1,2-glycol, trimethylolpropane, 4,4'-dihydroxy-diphenylpropane, aniline, ammonia, ethanolamine or ethylene diamine. Sucrose polyethers such as those described e.g. in German Auslegeschriften Nos. 1,176;358 and 1,064,938 may also be used. Polyethers modified with vinyl polymers, as can be obtained e.g. by polymerizing styrene and acrylonitrile in the presence of polyethers (U.S. Pat. Nos. 3,383,351; 3,304,273; 3,523,093 and 3,110,695 and German Patent Specification No. 1,152,536) are also suitable as are also polybutadienes which contain hydroxyl groups.

Among the polythioethers, there should be particularly mentioned the condensation products of thiodiglycol with itself and/or with other glycols, dicarboxylic acids, formaldehyde, aminocarboxylic acids or amino alcohols. The products obtained are polythio mixed ethers, polythio ether esters or polythio ether esteramides, depending on the cocomponents.

Suitable polyacetals are e.g. the compounds which can be prepared from glycols such as diethylene glycol, triethylene glycol, 4,4'-dioxethoxy-diphenyl dimethylmethane, hexanediol and formaldehyde. Polyacetals suitable for the purpose of the invention may also be prepared by polymerizing cyclic acetals.

Suitable polycarbonates with hydroxyl groups include those known per se which can be prepared by reacting diols such as propane-1,3-diol, butane-1,4-diol and/or hexane-1,6-diol, diethylene glycol, triethylene glycol or tetraethylene glycol with diaryl carbonates such as diphenyl carbonate or with phosgene. Suitable processes for preparing polycarbonates are taught by in *Chemistry and Physics of Polycarbonates*, by Hermann Schnell, Interscience Publishers, 1964.

Suitable polyester amides and polyamides include the predominantly linear condensates obtained from polyvalent saturated and unsaturated carboxylic acids or their anhydrides and polyvalent saturated and unsaturated amino alcohols, diamines, polyamines and mixtures thereof.

Polyhydroxyl compounds which already contain urethane or urea groups and modified or unmodified natural polyols such as castor oil, carbohydrates or starches may also be used. Addition products of alkylene oxides to phenol formaldehyde resins or urea formaldehyde resins are also suitable.

Other examples of higher molecular weight polyhydroxyl compounds may be found e.g. in High Polymers, Volume XVI, "Polyurethanes, Chemistry and Technology" by Saunders-Frisch, Interscience Publishers, New York, London, Volume I, 1962, pages 32–42 and pages 44–54 and Volume II, 1964, pages 5–6 and 198–199 and in Kunststoff-Handbuch, Volume VII, Vieweg-Höchtlen, Carl-Hanser-Verlag, Munich 1966, e.g. on pages 45 to 71.

Suitable low molecular weight polyhydroxyl compounds are, for example, the compounds mentioned above as suitable starting components for preparing the polyesters.

The polyisocyanates used as one-component reactive systems in the process according to the invention either as such or in the form of their reaction products with the above mentioned polyhydroxyl compounds may be aliphatic, cycloaliphatic, araliphatic, aromatic or heterocyclic. A detailed description of these polyisocyanates has been given by W. Siefken in Justus Liebigs Annalen der Chemie, 562, pages 75 to 136. The following are mentioned as examples; ethylene diisocyanate; tetramethylene-1,4-diisocyanate; hexamethylene-1,6-diisocyanate; dodecane-1,12-diisocyanate, cyclobutane-1,3-diisocyanate; cyclohexane-1,3- and 1,4-diisocyanate and any mixtures of these isomers; 1-isocyanato-3,3,5-trimethyl-5-isocyanatomethyl-cyclohexane (German Auslegeschrift No. 1,202,785); hexahydrotolylene-2,4-and -2,6-diisocyanate and any mixtures of these isomers, hexahydrophenylene-1,3- and/or -1,4-diisocyanate; perhydro-diphenylmethane-2,4'and/or -4,4'-diisocyanate; phenylene-1,3-and -1,4-diisocyanate; tolylene-2,4- and -2,6-diisocyanate and any mixtures of these isomers; diphenylmethane-2,4'- and/or -4,4'-diisocyanate; naphthylene-1,5-diisocyanate; triphenylmethane-4,4',4''-triisocyanate; polyphenyl-polymethylene polyisocyanates which can be obtained by anilineformaldehyde condensation followed by phosgenation and which have been described e.g. in British Patent Specifications Nos. 874,430, and 848,671; perchlorinated aryl polyisocyanates as described e.g. in German Auslegeschrift No. 1,157,601; polyisocyanates which contain carbodiimide groups as described in German Patent Specification No. 1,092,007; the diisocyanates described in U.S. Pat. No. 3,492,330; polyisocyanates containing allophanate groups according to British Patent Specification No. 994,890, Belgian Patent Specification No. 761,626 and published Dutch Patent Application No. 7,102,524; polyisocyanates which contain isocyanurate groups as described e.g. in German Patent Specification Nos. 1,022,789; 1,222,067 and 1,027,394 and in German Offenlegungsschriften Nos. 1,929,034 and 2,004,048; polyisocyanates containing urethane groups as described e.g. in Belgian Patent Specification No. 752,261 or in U.S. Pat. No. 3,394,164; polyisocyanates which contain acylated urea groups according to German Patent Specification No. 1,230,778; polyisocyanates which contain biuret groups as described e.g. in German Patent Specification No. 1,101,394; British Pat. No. 889,050 and French Patent Specification No. 7,017,514; the polyisocyanates prepared by telomerization reactions described e.g. in Belgian Patent Specification No. 723,640; polyisocyanates which contain ester groups such as those mentioned e.g. in British Patent Specification Nos. 956,474 and 1,072,956; U.S. Pat. No. 3,567,763 and in German Patent Specification No. 1,231,688 and reaction products of the above mentioned isocyanates with acetals according to German Patent Specification No. 1,072,385.

Particularly interesting for the process according to the invention are the non-volatile aliphatic and/or aromatic polyisocyanates or corresponding mixed types or various types of residue isocyanates obtained when commercial diisocyanates are processed by distillation. These products may, in addition, contain activators such as organometallic catalysts, for example, tin octoate and tertiary amines.

Polyisocyanates which are obtained by phosgenating aniline-formaldehyde condensates, by trimerizing polyisocyanates or by reaction of polyisocyanates with water or polyols under conditions which give rise to polyisocyanates with urethane, biuret, isocyanurate or allophanate structure are particularly preferred. In the process according to the invention, it is suitable to use mixtures of various such polyisocyanates because the various isocyanate components lower each other's melting points to form mixtures which are liquid at room temperature.

The various isocyanate containing compounds mentioned above are crosslinked by reacting with moisture after application to the constructional material according to the invention. Any extensive foaming by the liberation of carbon dioxide should be avoided, however, in order to guarantee a good mechanical strength of the products.

The substrate is preferably completely impregnated with the one-component reactive system mentioned above but it may also be only coated or wetted on the surface.

In order to achieve special effects with regard to stiffening or permeability of the constructional material, the material may be only partly impregnated or coated. If desired, the material in the form of a woven or non-woven web may be impregnated or coated on one side only so that it will then contain the reactive system only to a certain depth or only on one side. In some cases, it is advisable to impregnate or coat the substrate with other substances before or after it has been treated with the reactive system, for example in order to prevent the reactive system from penetrating too deeply into the substrate, to modify it or to protect the reactive system against mechanical or environmental damage after it has been introduced.

In the process according to the invention, the substrate may be supersaturated with the reaction system so that it also completely fills the gaps between the fibers or intercellular bridges and will exude from the substrate even under light pressure. Alternatively, the substrate may be provided with so little of the reactive system that it only just wets all or only part of the fibers, filaments or other surfaces of the substrate, e.g. the cell walls or filler particles. In the first mentioned case, the end products are substantially impermeable and, in the second case, they are substantially permeable to air, liquids or dust. By suitable choice of the quantities of reactive system used, these properties of the products produced from the constructional materials according to the invention can easily be controlled as desired.

Substrates which have been impregnated or coated according to the invention should preferably still have a certain permeability in order to provide rapid access for the moisture required for hardening the reactive system even into the deep parts of the substrate or of a package produced by winding this material. This can be achieved by, for example, only partly impregnating or coating the substrate, for example, by applying it in the form of a pattern, or by using a sufficiently small quantity of the reactive system.

The impregnation or coating process is carried out with conventional apparatus, for example, by application with a coating knife, steeping the material and then removing excess liquid either on rollers or by centrifuging, or applying the impregnating material by spraying, printing reversal processes or the like. The reactive material may be applied in the form of a solution or, in cases where it has a sufficiently low viscosity at room temperature or at an elevated temperatures, the pure, solvent-free material may be applied. It is preferred to work without any solvent.

Any solvents or other volatile components contained in the reactive systems used according to the invention are, however, removed at the latest after they have been applied to the substrate e.g. by means of a vacuum treatment.

In the process according to the invention, the substrates are generally used in a dried state and treated with the reactive system in sealed apparatus, preferably with the complete exclusion of atmosphere or in a very dry atmosphere, e.g. under nitrogen or noble gases.

After treatment of the constructional materials with the reactive system, they are stored in an air tight and moisture-free environment until they are applied. The constructional materials, which may be in the form of spools, wound packages, rolls or webs or even unformed, are preferably sealed into coated aluminum foils or other foils made of plastics which are very impermeable to moisture.

The materials according to the invention may, of course, also be stored in suitably sealed plastics or metal containers such as cans.

The following reactive systems were used in the examples which serve to explain but not restrict the nature of the new constructional materials:

EXAMPLES (A) Biuret polyisocyanate which has been prepared according to Example 2 of German Offenlegungsschrift No. 2,308,015 and U.S. Pat. No. 3,903,127 by reacting 11 mols of hexamethylene diisocyanate with 1 mol of tertiary butyl alcohol, at 160°–185° C. The product contains 23.3% by weight of isocyanate and has a viscosity of 2800 cP at 20° C. 6 parts by weight of Sn(II)-octoate per 100 parts of polyisocyanate are added before application to the substrate.

(B) Mixture of 30 parts by weight of tolylene-2, 4-diisocyanate (65% of 2,4- and 35% of 2,6-isomer) and 70 parts by weight of the isocyanate residue obtained from the commercial production of this diisocyanate. The mixture is dissolved to form a 50% solution in dichloromethane. The solution has an isocyanate content of 12.5%.

By isocyanate residue is meant in this case a material which has been obtained as residue (sump) in the commercial distillation of tolylene diisocyanate and which cannot be distilled at 180° C. at a pressure of 10–15 mm Hg.

(C) Polyester urethane with an average molecular weight of 2900 and —Si—(OC$_2$H$_5$)$_3$ end groups. The polyester urethane is prepared by reacting an isocyanate-prepolymer from 1 mol of adipic acid/diethylene glycol polyester (hydroxyl number 56) and 2 mols of hexamethylene diisocyanate with 2 mols of N-cyclohexyl-aminomethyl triethoxysilane.

EXAMPLE 1

The following general method of procedure was employed: The reactive material is introduced into a vat in a liquid-viscous form. A substrate web which has been pre-dried in a vacuum at 80° C. is passed through this vat to impregnate it and then freed from excess reactive material by passing it through a pair of rollers. The impregnated substrate web is then passed through a degasification tunnel in which the last residues of volatile constituents are removed at a vacuum of about 1 Torr at 20° C. The impregnated substrate is then wound or rolled up and finally sealed in a polyethylene-coated aluminum foil in a packaging machine. The whole apparatus is arranged in a closed chamber which is filled either with dehydrated air or with dehydrated nitrogen.

This method is used for impregnating gauze bandages, non-woven perlon webs, paper webs, glass fabric webs and webs of polyurethane soft foam foils with the above mentioned reactive materials, A, B and C.

The application of the material will now be described, using as the example gauze bandages which have been treated according to the invention and removed from their sealed package after 4 weeks. They can easily be rolled up to be wound around a mandrel of wire mesh covered with a cotton cloth. The layers of the winding stick together due to the tackiness of the materials. No unpleasant odor or other unpleasant effect due to the chemicals used could be noted. The room in which the material was applied had a relative atmospheric moisture of about 65%.

None of the wound materials prepared in this way were still sticky after 1 hour. After 3 hours, the wound material, impregnated with reactive system A, could be removed from the mandrel and, after about 10 hours, it had reached its final state of firmness. The corresponding times are 0.5 hours and 2.5 hours in the case of B and 0.3 hours and 2 hours in the case C.

When hardened, the wound materials are stable tubes with air-permeable walls, as can be clearly demonstrated e.g. by blowing tobacco smoke through them.

Wound packages of this kind are suitable, for example, for replacing the conventional rather heavy and impermeable plaster of Paris bandages, especailly because they are more permeable to air than conventional bandages.

EXAMPLE 2

A soft polyurethane foam is first prepared as a substrate in known manner by vigorously mixing the following components:
100 parts by weight of a polyether which has been prepared by the addition of 87% by weight of propylene oxide and 13% by weight of ethylene oxide to trimethylolpropane (hydroxyl number 35),
4 parts by weight of water,
0.15 parts by weight of triethylene diamine,
0.35 parts by weight of tin (II) dioctoate,
1 part by weight of foam stabilizer (polyether polysiloxane)
5 parts by weight of monofluorotrichloromethane and
4.8 parts by weight of tolylene diisocyanate (80% of 2,4- and 20% of 2,6-isomer).

A soft polyurethane foam with about 95% of open cells and a density of 25 kp/m$^3$ is obtained. A sheet of this soft foam measuring 3×10×100 cm is impregnated with a solution composed of 50 parts by weight of a sump residue with a molecular weight of about 1000 which contains isocyanate groups from the distillation of a tolylene diisocyanate which has an isomeric ratio of 65 parts by weight of 2,4-isomer and 35 parts by weight of 2,6-isomer, and 50 parts by weight of dichloromethane. The solution used has an isocyanate content of 12,5% and a viscosity of 10 oP when measured in a Hoeppler-viscosimeter at 20° C. When this procedure is employed, the polyurethane matrix swells spontaneously by about 90% of its original volume and, at the same time, the remaining cell walls are burst open.

The excess solution is squeezed off by centrifuging at 600 revs. per min. for 3 minutes. The solvent then still remaining in the foam is removed by applying a vacuum of 0.1 mm Hg at 22° C., the increase in volume being thereby reduced to about 10%. The impregnated foam sheet is rolled up and sealed into a polyethylene coated aluminum foil.

After 6 weeks' storage, the package is opened and the foam web rolled. When exposed to a room temperature of about 20° C. and relative atmospheric humidity of 65%, the soft material becomes hard within about 3 hours. The total increase in weight is about 380%.

Although the invention has been described in detail for the purpose of illustration, it is to be understood that such detail is solely for that purpose and that variations can be made therein by those skilled in the art without departing from the spirit and scope of the invention except as it may be limited by the claims.

What is claimed is:

1. A synthetic resin based substitute for plaster of paris medical bandaging or splinting material enclosed in a moisture-free and moisture impervious package comprising
   (a) a flexible fiberglass substrate coated or impregnated with
   (b) a reactive one-component system which is based on an aromatic polyisocyanate which:
      (1) is free of oxycarbonyl isocyanate groups, urethane groups, urea groups, biuret groups and allophanate groups;
      (2) contains less than about 1% by weight of volatile components which can be removed at 12 Torr and 20° C. in one hour;
      (3) renders said impregnated or coated flexible fiberglass substrate into a rigid self-supporting structure of comparable mechanical strength to plaster of paris materials free of extensive foaming by reaction with water after forming into a planar or hollow configuration; and
      (4) contains a sufficient amount of a catalyst for the reaction of isocyanate groups with water to give it a hardening time suitable for a substitute for plaster of paris medical bandaging or splinting materials,
said impregnated or coated fiberglass substrate remaining formable in storage.

2. A flexible, workable medical bandaging or splinting material enclosed in a moisture-free, moisture-impervious package which is stable in storage and which forms a rigid self-supporting structure free of extensive foaming upon reaction with water comprising a flexible substrate impregnated or coated with a reactive one-component system containing no oxycarbonyl isocyanate groups comprising a polyisocyanate.

3. A flexible, workable medical bandaging or splinting material enclosed in a moisture-free, moisture-impervious package is stable in storage and which forms a rigid self-supporting structure free of extensive foaming upon reaction with water comprising a flexible substrate impregnated or coated with a reactive one-component system containing no oxycarbonyl comprising a polyisocyanate with aromatically bound isocyanate groups.

4. A flexible, workable medical bandaging or splinting material enclosed in a moisture-free, moisture-impervious package which is stable in storage and which forms a rigid self-supporting structure of comparable mechanical strength to plaster of paris materials free of extensive foaming after forming into a planar or hollow configuration by reaction with water comprising a flexible substrate impregnated or coated with a reactive one-component system comprising a polyisocyanate free of oxycarbonyl isocyanate groups and containing sufficient catalyst for the reaction of isocyanate groups with water to give it a hardening time suitable for a substitute for plaster of paris medical bandaging or splinting materials.

5. A flexible, workable medical bandaging or splinting material enclosed in a moisture-free and moisture impervious package which remains formable in storage and which forms a rigid self-supporting structure of comparable mechanical strength to plaster of paris materials free of extensive foaming after forming by reaction with water comprising a flexible fiberglass substrate impregnated or coated with a reactive one-component system comprising a polyisocyanate free of oxycarbonyl isocyanate groups and containing sufficient catalyst for the reaction of isocyanate groups with water to give it a hardening time suitable for a substitute for plaster of paris medical bandaging or splinting materials.

6. The medical bandaging or splinting material of claim 5 wherein the polyisocyanate is free of urethane and urea groups.

7. The medical bandaging or splinting material of claim 6 wherein the polyisocyanate is free of biuret and allophanate bonds.

8. The medical bandaging or splinting material of claim 7 wherein the polyisocyanate is based on the phosgenation product of an aniline formaldehyde condensation.

9. The medical bandaging or splinting material of claim 8 wherein the polyisocyanate is the diphenylmethane diisocyanate distillation product of the phosgenation which has been partially carbodiimidized.

10. The medical bandaging or splinting material of claim 8 wherein the polyisocyanate is the mixture of polymethylene polyisocyantes and the 2,2'-, 2,4'- and 4,4'-isomers of diphenylmethane diisocyanate obtained as a distillation residue of the phosgenation.

11. The medical bandaging or splinting material of claim 8 wherein the polyisocyanate is diphenylmethane diisocyanate.

12. The medical bandaging or splinting material of claim 7 wherein the polyisocyanate is based on the phosgenation product of toluene diamine.

13. The medical bandaging or splinting material of claim 12 wherein the polyisocyanate is the distillation residue obtained in the commercial production of toluene diisocyanate.

14. The medical bandaging or splinting material of claim 12 wherein the polyisocyanate is toluene diisocyanate.

15. The medical bandaging or splinting material of claim 12 wherein the polyisocyanate is a mixture of the distillation residue obtained in the commercial production of toluene diisocyanate and toluene diisocyanate itself.

16. The medical bandaging or splinting material of claim 7 wherein the polyisocyanate has aromatically bound isocyanate groups.

17. The medical bandaging or splinting material of claim 7 wherein the impregnated or coated fiberglass substrate contains less than about 1% by weight of volatile compounds which can be removed at 12 Torr and 20° C. in one hour.

* * * * *